United States Patent [19]
Kelkar et al.

[11] Patent Number: 5,877,354
[45] Date of Patent: Mar. 2, 1999

[54] PROCESS FOR MAKING ISOPHORONE WITH IMPROVED COLOR AND COLOR STABILITY

[75] Inventors: Chandrashekhar P. Kelkar, Plum Boro, Pa.; Alain A. Schutz, Furnaux, Belgium

[73] Assignee: Aristech Chemical Corporation, Pittsburgh, Pa.

[21] Appl. No.: 984,117

[22] Filed: Dec. 3, 1997

[51] Int. Cl.[6] .................................................. C07C 45/78
[52] U.S. Cl. ........................... 568/360; 568/350; 568/377
[58] Field of Search .................................... 508/340, 343, 508/366, 350, 360, 377

[56] References Cited

U.S. PATENT DOCUMENTS

| | | | |
|---|---|---|---|
| 4,248,673 | 2/1981 | Cheminal et al. | 568/376 |
| 4,434,301 | 2/1984 | Papa | 568/366 |
| 5,276,197 | 1/1994 | Nosberger et al. | 568/341 |
| 5,352,839 | 10/1994 | Grebinoski et al. | 568/366 |
| 5,627,303 | 5/1997 | Braithwaite et al. | 568/388 |
| 5,728,891 | 3/1998 | Bueschken et al. | 568/376 |

*Primary Examiner*—James H. Reamer
*Attorney, Agent, or Firm*—Robert R. Gavlik

[57] ABSTRACT

The present invention is a process for the production of isophorone having improved color and color stability. Crude isophorone is selectively hydrogenated to remove color forming impurities. The product isophorone will have an APHA color of about 10 or less.

6 Claims, No Drawings

PROCESS FOR MAKING ISOPHORONE WITH IMPROVED COLOR AND COLOR STABILITY

TECHNICAL FIELD

This invention relates to a process for refining crude isophorone, and particularly to a process for producing isophorone with improved color and improved color stability.

The present invention provides for the removal of color contaminants which cannot be separated by typical fractionation methods. Crude isophorone is refined to produce a product with low color and improved color stability.

BACKGROUND OF THE INVENTION

Isophorone is an industrial solvent prepared by aldol condensation of acetone. The reaction is carried out in a homogenous media with an alkali hydroxide catalyst or in a heterogeneous media with a mixed oxide catalyst derived from oxides of magnesium and aluminum, or calcium and aluminum. Freshly distilled isophorone has a APHA color of 20–30 [as measured by ASTM Standard Test Method for Color of Clear Liquids (Platinum-Cobalt Scale)] but degrades with time to APHA values of 100 or higher. Further it is found that the color deterioration accelerates when the product is stored at elevated temperatures.

Some of the by products made during the synthesis of isophorone have boiling points which are very close to isophorone and therefore are not easily removed by simple distillation. Some of these compounds are responsible for giving the isophorone product a distinct yellow color which may be undesirable.

There are several techniques known in the art to remove color from isophorone. U.S. Pat. No. 2,204,956 discloses a process for purifying ketones. The process includes the addition of ammonia followed by distillation. U.S. Pat. No. 2,968,677 discloses a method of treating colored isophorone with an aromatic sulfonic acid and distilling the isophorone from the mixture. U.S. Pat. No. 4,059,632 discloses the discolorization of isophorone by treatment with phosphoric acid for at least seven hours at 130°–190° C. U.S. Pat. No. 4,248,673 describes a method of treating crude isophorone with acid exchange resins followed by neutralization with excess alkaline reagent and washing to remove the salts formed, and followed by fractionation to purify the isophorone. U.S. Pat. No. 4,434,301 describes a method which comprises contacting crude isophorone with a strong caustic aqueous solution at a temperature of about 140°–200° C. for about for about 1–2 hours, washing the treated isophorone with water and then recovering decolorized isophorone by fractional distillation.

All the above prior art methods require treatment with acidic or basic reagents which necessitate a washing/neutralization stage before the treated isophorone can be distilled. They are also very capital intensive processes which require holding tanks for treatment followed by washing tanks and the need for disposal of the neutralized effluent. Also, all the above methods lead to loss of isophorone yield to products which are not useful.

It is the object of the present invention to produce substantially color free isophorone by a method which is much less capital intensive.

It is also an object of the present invention to produce isophorone which not only has superior color, but superior color stability.

SUMMARY OF THE INVENTION

The present invention discloses a method for producing isophorone with low color by selectively hydrogenating color forming impurities at low temperatures. The hydrogenation can be carried out at a low enough temperature and high space velocity so as to limit the hydrogenation of isophorone which can result in a loss of yield.

Freshly distilled isophorone has a typical composition of 99.5% isophorone, 0.3% beta-isophorone, 0.1% phorones and 0.1% xylitones and has a APHA color of 20–30. The predominant color forming impurities are linear phorones. These phorone isomers have boiling points very close to isophorone and cannot be easily removed by fractionation.

The crude isophorone is hydrogenated in the presence of a hydrogenation catalyst. Most common are catalysts comprising Cu, Ni, Pd or Pt. Typically, these are supported on a medium such as alumina. The impurities are selectively hydrogenated with little loss of isophorone.

DETAILED DESCRIPTION OF THE INVENTION

A method is disclosed for discolorization of freshly distilled isophorone by selectively hydrogenating the color forming impurities to saturated compounds.

Crude isophorone is passed over a hydrogenation catalyst in the presence of hydrogen at temperatures typically between 10°–80° C., LHSV usually between 1–10 $hr^{-1}$ and a pressure typically less than 100 psig. Preferably, the catalyst comprises Cu, Ni, Pd or Pt. More preferably, the catalyst comprises Pd, and most preferably is a fixed bed Pd/alumina catalyst. The hydrogenation product will have an APHA color of about 10 or less, and depending on conditions, will comprise 1–5 wt. % of 3,3,5 trimethyl cyclohexanone (TMC). It should be noted that in the context of the present invention, an APHA reading below 10 is reported as 10. This is due to the fact that below 10, APHA readings are difficult to obtain without very precise equipment. An APHA reading of 10 or lower will yield a superior product compared to typical commercial grade isophorone. However, it is believed that the present invention will yield an APHA color far below 10.

An advantage of the present invention is that the by-product TMC has commercial value of its own, and can be easily removed via distillation from isophorone and sold as a separate product. However, in many applications where low color for isophorone is desired the presence of small quantities (~2%) of TMC is not a hindrance and hence need not be removed from the final product.

Again, the choice of the hydrogenation catalyst is not critical but Pd based catalysts are the most preferred. The choice of process conditions are also not critical; the overall attempt being to limit the hydrogenation of isophorone to TMC. Lower temperatures, lower pressures, lower hydrogen/isophorone molar ratio and higher space velocities will lower the formation of the TMC by-product. The reactor can be operated at a temperature less than 80° C. with temperatures of about 15°–35° C. being preferred. Although it is possible to operate the reactor under cryogenic conditions, it is most economical industrially to operate the reactor at room temperature. Since very small amounts of impurities are being hydrogenated, the ratio of hydrogen to isophorone can be less than unity. Preferably, it is at least about 0.01, and most preferably about 0.01 to about 1. A smaller hydrogen/isophorone ratio, in addition to limiting TMC formation, may also lower operational costs by avoiding recycling of unused hydrogen. The space velocity at which the crude isophorone is fed to the reactor is also not critical and the highest possible space velocity should be used, which would result in the smallest reactor size. The most preferred space velocity is in the range 1–10 hr$^{-1}$.

Since the formation of small amounts of TMC is inherent, the invention has the operational flexibility whereby the severity of the finishing step can be easily manipulated to produce both isophorone with good color and TMC as a deliberate by-product. This can be achieved simply by increasing the reactor temperature.

Color can also be measured by spectrophotometric method at 400 nm. The percent transmittance through the sample is inversely proportional to color. Since one is a visual method and the other is spectrophotometric method at a specific wavelength a linear correlation does not exist between color numbers reported by the two methods. Both methods through are valid and useful for measuring trends in color change. Color measurements by both methods are reported in the Tables that follow.

The invention is illustrated, but not limited by the following Example:

EXAMPLE 1

Freshly distilled isophorone was selectively hydrogenated to substantially color free isophorone under the following conditions:

Catalyst: 0.5% Pd/Alumina, ⅟₁₆" spheres

Catalyst volume: 30 cc

Isophorone feed: 186 cc/h

Hydrogen feed: 100 cc/min

Reactor temperature: 25° C.

Reactor pressure: 20 psig

The results are reported in Tables I–III below.

TABLE I

|  | Reactor feed (%) | Reactor Effluent (%) |
|---|---|---|
| Beta-isophorone | 0.29 | 0.0 |
| TMC | 0.0 | 1.2 |
| Phorone | 0.14 | 0.0 |
| Isophorone | 99.49 | 98.4 |
| Xylitones | 0.08 | 0.05 |
| Other | 0 | 0.35 |
| Color (APHA) | 20 | 10 |
| Color (% Transmittance) | 60 | 97 |

The reactor feed and the reactor effluent were tested for color stability at 25° and 35° C. The results are as follows.

TABLE II

Color Stability of Reactor Feed and Reactor Effluent at 25° C.

| | Reactor Feed | | Reactor Effluent | |
|---|---|---|---|---|
| Days | APHA color method | % Transmittance | APHA color method | % Transmittance |
| 0 | 20 | 60 | 10 | 97 |
| 3 | 20 | 58 | 10 | 89 |
| 5 | 20 | 58 | 10 | 89 |
| 10 | 20 | 57 | 10 | 88 |

TABLE II-continued

Color Stability of Reactor Feed and Reactor Effluent at 25° C.

| | Reactor Feed | | Reactor Effluent | |
|---|---|---|---|---|
| Days | APHA color method | % Transmittance | APHA color method | % Transmittance |
| 14 | 20 | 56 | 10 | 88 |
| 17 | 20 | 56 | 15 | 85 |
| 21 | 25 | 55 | 20 | 82 |
| 28 | 25 | 54 | 20 | 76 |

Table III

Color Stability of Reactor Feed and Reactor Effluent at 35° C.

| | Reactor Feed | | Reactor Effluent | |
|---|---|---|---|---|
| Days | APHA color method | % Transmittance | APHA color method | % Transmittance |
| 0 | 20 | 60 | 10 | 97 |
| 2 | 20 | 58 | 15 | 82 |
| 5 | 25 | 55 | 20 | 80 |
| 9 | 25 | 53 | 20 | 75 |
| 16 | 30 | 49 | 20 | 70 |

As can be seen from Tables II and III, the effluent isophorone not only possesses superior color properties, but also possesses superior color stability compared to typical isophorone.

We claim:

1. A process for refining crude isophorone comprising hydrogenating a composition comprising said crude isophorone and at least one color forming impurity in the presence of a hydrogenation catalyst at a pressure of about 100 psig or less, and at a temperature of about 10°–80° C., and at a LHSV for said composition of about 1–10 hr$^{-1}$, wherein said color forming impurity is selectively hydrogenated to produce a product isophorone, said product isophorone having an APHA color of less than 10.

2. A process according to claim 1 further comprising the step of recovering the product isophorone.

3. A process according to claim 1 wherein the hydrogenation catalyst comprises a metal selected from the group consisting of Pd, Ni, Cu and Pt.

4. A process according to claim 1 wherein the catalyst is a Pd/alumina catalyst.

5. A process according to claim 1 wherein a hydrogen to isophorone molar ratio is at least about 0.01.

6. A composition comprising a refined isophorone having an APHA color of less than 10, said composition made from the process comprising hydrogenating a composition comprising a crude isophorone and at least one color forming impurity in the presence of a hydrogenation catalyst at a pressure of about 100 psig or less, and at a temperature of about 10°–80° C. and at a LHSV for said composition of about 1–10 hr$^{-1}$, wherein said color forming impurity is selectively hydrogenated to produce a hydrogenation product comprising said refined isophorone.

* * * * *